(12) United States Patent
Shimoda

(10) Patent No.: US 7,428,049 B2
(45) Date of Patent: Sep. 23, 2008

(54) APPARATUS AND METHOD FOR INSPECTING FILM DEFECT

(75) Inventor: Kazuhiro Shimoda, Odawara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/759,976

(22) Filed: Jun. 8, 2007

(65) Prior Publication Data

US 2007/0285665 A1 Dec. 13, 2007

(30) Foreign Application Priority Data

Jun. 9, 2006 (JP) .............................. 2006-161280

(51) Int. Cl.
*G01J 4/00* (2006.01)
(52) U.S. Cl. ...................................... 356/364
(58) Field of Classification Search ........................ None
See application file for complete search history.

(56) References Cited

U.S. PATENT DOCUMENTS

2001/0021016 A1* 9/2001 Shimoda .................. 356/239.1

FOREIGN PATENT DOCUMENTS

| JP | 6-235624 A | 8/1994 |
| JP | 8-54351 A | 2/1996 |
| JP | 9-73081 A | 3/1997 |
| JP | 11-30591 A | 2/1999 |
| JP | 2001-324453 A | 11/2001 |

* cited by examiner

*Primary Examiner*—Roy M Punnoose
(74) *Attorney, Agent, or Firm*—Sughrue Mion, PLLC

(57) ABSTRACT

First and second polarizing plates are placed to be crossed nicols across a film to be inspected. A light source projects light toward the film through the first polarizing plate. A light receiver receives the light transmitted through the film and the second polarizing plate. When θ1 represents an angle formed between an optical axis of the light receiver and a normal line that is perpendicular to the film surface, and θ2 represents a rotational angle formed between the optical axis and a reference line that is orthogonal to a slow axis of the film, the light receiver is positioned to satisfy the following conditions:

$15° \leq \theta1 \leq 35°$, $20° \leq \theta2 \leq 60°$.

15 Claims, 12 Drawing Sheets

$\phi = 3.2°$ $\phi = 4.8°$ $\phi = 11.8°$
NOT DETECTABLE
NOT DETECTABLE

APPARATUS AND METHOD FOR INSPECTING FILM DEFECT

FIELD OF THE INVENTION

The present invention relates to a film defect inspection apparatus and a film defect inspection method, for inspecting defects of a film based on light transmitted through the film.

BACKGROUND OF THE INVENTION

Optical compensation film, or retardation film, is known as a device for improving viewing angle of a liquid crystal display device. The optical compensation film is produced by forming an alignment film on a long web of transparent film, and then forming an optically anisotropic liquid crystalline compound layer by spreading and drying a liquid crystalline compound on the alignment film, as disclosed for example in Japanese Patent Laid-open Publication No. 9-73081.

The optical compensation film as described above may have defects caused by various factors during the manufacturing processes. The defects of the optical compensation film having the liquid crystalline compound layer are, for example, luminescent spot defects due to mixture or adhesion of extraneous matters in the liquid crystal layer, repellent defects where the liquid crystalline compound layer cannot be partially formed on the film as a support, film unevenness due to irregularity of molecular orientation, and the like. In addition, thickness unevenness of the film as the support is also the defect of the optical compensation film. Although the manufacturing processes for the optical compensation film are strictly supervised, it is hard to exterminate the defects of the produced film. For this reason, it is necessary to perform an inspection during the manufacture to locate the defective positions on the optical compensation film.

The defect inspection of the optical compensation film on the manufacturing line may be called the on-line inspection, and there are many conventional methods for the on-line inspection.

For example, Japanese Patent Laid-open Publication No. 6-235624 suggests an inspection method, wherein an inspection light beam is projected from a light source toward a target transparent film as being conveyed, and the reflected or transmitted light beam is received on a linear sensor. Based on the received light beam, fine unevenness of the film surface, extraneous matters or air bubbles in the film, or protuberances produced on an antireflective coat on the film surface can be automatically detected at a high speed.

Japanese Patent Laid-open Publication No. 8-54351 discloses a defect inspection method, wherein a high-luminous high-directional light beam is projected at an angle of 5° to 15° onto a surface of a transparent sheet as being conveyed continually, and light transmitted through the transparent sheet is captured by a camera, so as to detect the film defect based on data obtained by image-processing an output signal from the camera. This method enables detecting fine unevenness of the film thickness, i.e. unevenness of 0.1 µm to 5 µm deep and 0.1 µm to 10 µm wide.

Japanese Patent Laid-open Publication No. 11-30591 discloses a method, wherein a light source and a camera are placed in opposition to each other across a film to be inspected, and one polarizing plate is placed between the light source and the film, whereas another polarizing plate is placed between the camera and the film. The film defect is detected based on an output signal from the camera. The displacement in the polarizing direction of the polarizing plates is set to be not more than ±20°. Thereby, vertically polarized components, which are generated by irregular orientation of film molecular or slight distortion of the film, are reduced, so texture signals are lowered and local changes in transmitted light amount through the film are reduced. Then, a change in polarizing condition that occurs at a defective position is made apparent as a dark area signal.

U.S. Patent Application Publication No. US 2001/0021016 (corresponding to Japanese Patent Laid-open Publication No. 2001-324453) discloses a method, wherein a pair of polarizing plates is placed to interpose a film to be inspected. The polarizing plates are parallel to the film. An intersection angle formed between a slow axis of the film and a polarizing transmission axis of one of the polarizing plates is set to be not less than 5° and not more than 15°. In order to eliminate viewing angle dependence, an optical compensation film practically equivalent to the film to be inspected is rotated through 180° along a plane corresponding to the film surface, or reversed front side to back side, and placed between the film and one of the polarizing plates. Fine optical defects can be detected by receiving light on a CCD camera in the normal line direction of the film surface.

When the optical compensation film, especially the optical compensation film having the liquid crystalline compound layer formed thereon, has the luminescent spot defect due to mixture or adhesion of extraneous matters in the liquid crystal layer, molecular orientation of the liquid crystal layer becomes highly irregular. Therefore, the luminescent spot defect can be readily detected by placing the optical compensation film to be inspected between the polarizing plates whose polarizing transmission axes are orthogonal to each other, and photographing the film in the normal line direction of the film with a camera and the like. The repellent defect where the liquid crystalline compound layer cannot be partially formed on the transparent film can also be easily detected in the same manner. In recent years, liquid crystal display devices have higher luminous and higher definition. Along with this trend, film unevenness with low brightness that could hardly be viewed needs to be detected as an appearance defect. Such film unevenness is caused by, for example, localized misalignment of an optic axis of the liquid crystal layer, and could not be detected by photographing the film in the normal line direction thereof with a camera and the like.

SUMMARY OF THE INVENTION

It is an object of the present invention to provide a film defect inspection apparatus and a film defect inspection method, which can detect unevenness of a film that is used as an optical compensation film and the like.

To achieve the above object, the present invention suggests a defect inspection apparatus for detecting defects of a film, the apparatus includes a pair of polarizing plates, a light source, a light receiver, and a judging device. The pair of polarizing plates is placed to be crossed nicols at both sides of the film and parallel to front and rear surfaces of the film. A polarizing transmission axis of one of the polarizing plates is approximately parallel to a slow axis of the film. The light source projects light onto one of the surfaces of the film through one of the polarizing plates. The light receiver is placed at an opposite side of the film to the light source. The light receiver firstly receives the light projected from the light source and transmitted through the film and the other one of the polarizing plates, and then outputs a photoelectric signal corresponding to the received light. The judging device judges based on the photoelectric signal from the light receiver as to whether there is a defect in the film or not. When $\theta 1$ represents an angle formed between an optical axis of the light receiver and a normal line that is perpendicular to the surfaces of the film, and θ2 represents a rotational angle formed between the optical axis and a reference line that is orthogonal to the slow axis of the film, the light receiver is positioned to satisfy the following conditions: 15°≦θ1≦35°, 20°≦θ2≦60°.

The film may be a positive or negative uniaxial birefringence film whose optic axis is inclined with respect to the normal line. The film may be a positive or negative uniaxial birefringence film having a liquid crystalline compound layer whose optic axis is inclined with respect to the normal line.

Orthogonal transmittance of the pair of polarizing plates is preferably low as much as possible. Average orthogonal transmittance of the pair of polarizing plates to light having wavelength of 500 nm to 750 nm is preferably not more than 0.027%. Orthogonal transmittance of the pair of polarizing plates to light having wavelength of 750 nm is more preferably not more than 0.030%.

The present invention also suggests a defect inspection apparatus for detecting defects of a film having a polarizing layer formed on one surface thereof. A polarizing transmission axis of the polarizing layer is approximately parallel to a slow axis of the film. The apparatus includes a polarizing plate, a light source, a light receiver, and a judging device. The polarizing plate is placed at an opposite side of the film to the polarizing layer. The polarizing plate is placed to be crossed nicols with the polarizing layer. The light source projects light onto one surface of the film. It is also possible that the light source projects the light onto the other surface of the film through the polarizing plate. The light receiver is placed at an opposite side of the film to the light source. The light receiver firstly receives the light projected from the light source and transmitted through the film and the polarizing plate. It is also possible that the light receiver firstly receives the light projected from the light source and transmitted through the film only. The light receiver then outputs a photoelectric signal corresponding to the received light. The judging device judges based on the photoelectric signal from the light receiver as to whether there is a defect in the film or not. When θ1 represents an angle formed between an optical axis of the light receiver and a normal line that is perpendicular to the surfaces of the film, and θ2 represents a rotational angle formed between the optical axis and a reference line that is orthogonal to the slow axis of the film, the light receiver is positioned to satisfy the following conditions: 15°≦θ1≦35°, 20°≦θ2≦60°.

The film may be a positive or negative uniaxial birefringence film whose optic axis is inclined with respect to the normal line. The film may be a positive or negative uniaxial birefringence film having a liquid crystalline compound layer whose optic axis is inclined with respect to the normal line. The liquid crystalline compound layer is formed on an opposite side of the film to the polarizing layer.

Orthogonal transmittance of the polarizing layer and the polarizing plate is preferably low as much as possible. Average orthogonal transmittance of the polarizing layer and the polarizing plate to light having wavelength of 500 nm to 750 nm is preferably not more than 0.027%. Orthogonal transmittance of the polarizing layer and the polarizing plate to light having wavelength of 750 nm is more preferably not more than 0.030%.

When the film is the negative uniaxial birefringence film, the light receiver is preferably placed at the rotational angle θ2 within an area that resides on the same side, from the slow axis of the film, as an optic axis of the film being orthogonally projected.

When the film is the positive uniaxial birefringence film, the light receiver is preferably placed at the rotational angle θ2 within an area that resides on the opposite side, from the slow axis of the film, as the optic axis of the film being orthogonally projected.

The light receiver includes a taking lens and a line image sensor having a large number of photo sensors arranged in a line. The line of the photo sensors is preferably inclined by the rotational angle θ2 with respect to the slow axis of the film. Moreover, a maximum angle formed between the optical axis of the light receiver and a line that connects the taking lens with one of longitudinal ends of an inspection area defined on the film is preferably in the range of 3° to 10°, and more preferably in the range of 3° to 5°.

The present invention suggests a defect inspection method for detecting defects of a film, the method includes the steps of projecting light onto one of front and rear surfaces of the film through one of polarizing members, the polarizing members being placed to be crossed nicols at both sides of the film, the polarizing members being parallel to the surfaces of the film, a polarizing transmission axis of one of the polarizing members being approximately parallel to a slow axis of the film; receiving the light projected onto and transmitted through the film with use of a light receiver; and judging based on the light received on the light receiver as to whether there is a defect in the film or not. When θ1 represents an angle formed between an optical axis of the light receiver and a normal line that is perpendicular to the surfaces of the film, and θ2 represents a rotational angle formed between the optical axis and a reference line that is orthogonal to the slow axis of the film, the light receiver is positioned to satisfy the following conditions: 15°≦θ1≦35°, 20°≦θ2≦60°.

According to the present invention, the pair of polarizing members, such as the polarizing plate or the polarizing layer, is placed parallel to the front and rear surfaces of the film, and at the same time, these polarizing members are placed to be crossed nicols across the film. The light is projected onto one surface of the film through one of the polarizing members. The light then passes through the other one of the polarizing members and is received on the light receiver. At this time, the light receiver is positioned to satisfy the following conditions: 15°≦θ1≦35°, 20°≦θ2≦60°, where θ1 represents the angle formed between the optical axis of the light receiver and the normal line that is perpendicular to the surfaces of the film, and θ2 represents the rotational angle formed between the optical axis and the reference line that is orthogonal to the slow axis of the film. Owing to this, fine film unevenness, which is generated due to misalignment of the optic axis of the film, can be accurately detected.

BRIEF DESCRIPTION OF THE DRAWINGS

The above and other objects and advantages will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
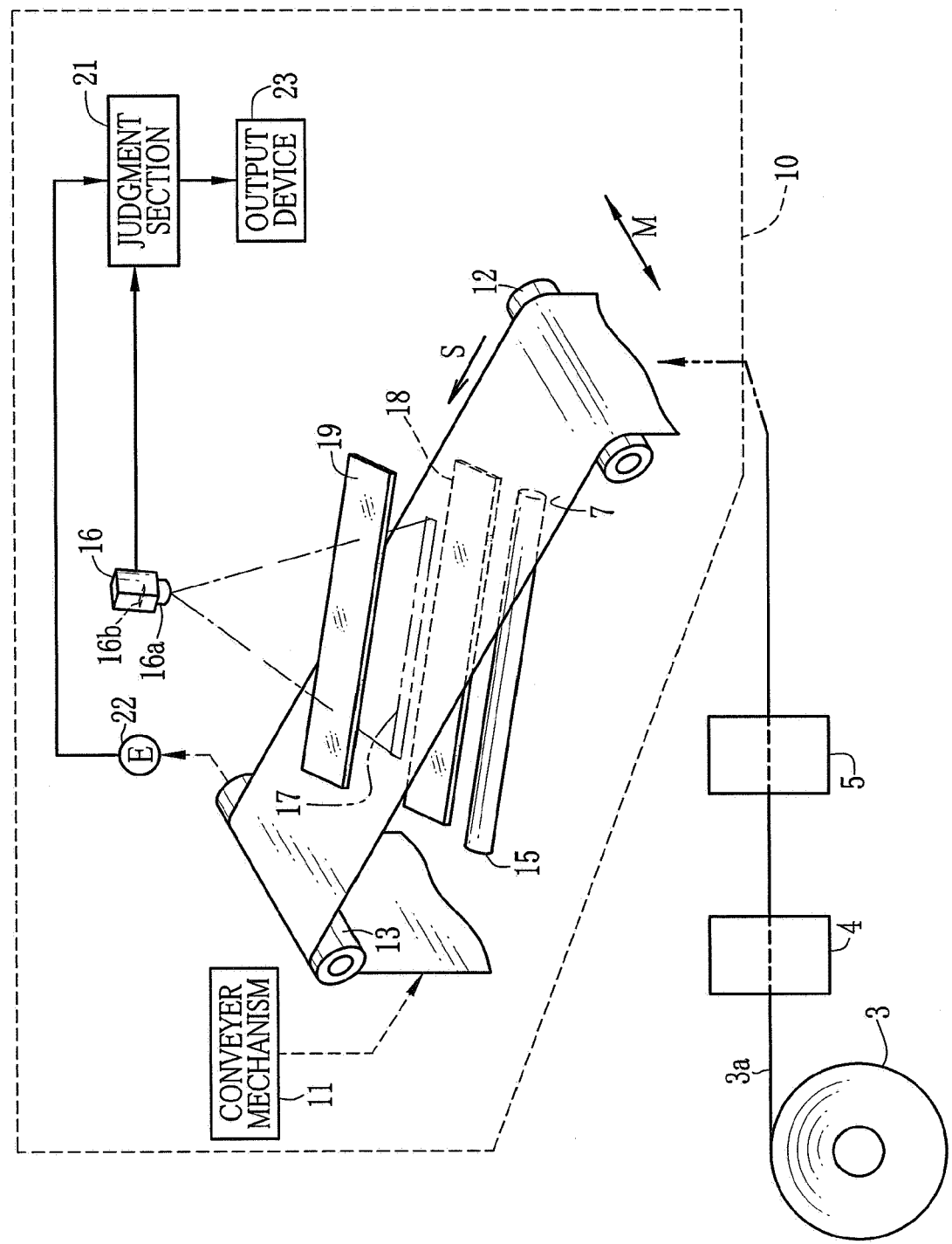
FIG. 1 is a schematic diagram illustrating a defect inspection apparatus to which the present invention is applied.

A first embodiment of the present invention is now explained. In FIG. 1, a long web of transparent resin film 3a is fed out from a film roll 3, and is fed into an alignment layer forming device 4. The alignment layer forming device 4 spreads a coating liquid, which contains a resin for forming an alignment layer, on the film 3a, and dries the coating liquid by heating, to form a resin layer for the alignment layer. The resin layer on the transparent resin film 3a is processed into an alignment layer through a rubbing treatment. Thereafter, the film 3a is fed to a liquid crystal layer forming device 5.

The liquid crystal layer forming device 5 spreads a coating liquid containing a liquid crystalline compound over the alignment layer of the transparent resin film 3a, evaporates a solvent of the coating liquid, and then heats the film 3a up to a liquid crystalline phase forming temperature, thereby to form a liquid crystal layer. Thereafter, ultraviolet rays are projected onto the liquid crystal layer to bridge it. In this way, the transparent resin film 3a with the liquid crystal layer, i.e., a transparent retardation film is manufactured. The retardation film is utilized as a transmissive-type optical compensation film for improving viewing angle of a liquid crystal display device.

A defect inspection apparatus 10 of the present invention is used for inspecting a film sheet 7, including the retardation film manufactured in the way as above. The defect inspection apparatus 10 is designed to detect film unevenness due to irregularity of molecular orientation (optic axis misalignment) of the liquid crystal layer. Hereinafter, the film unevenness is referred to as defect.

The film sheet 7 is not limited to the film having the liquid crystal layer formed thereon as manufactured in the way as above, but may be an optically anisotropic positive or negative uniaxial birefringence film whose optic axis is inclined with respect to a normal line of the film surface. Examples of the negative uniaxial birefringence film are a film having a layer of discotic liquid crystals, a uniaxial orientation polystyrene film, and the like. Examples of the positive uniaxial birefringence film are a film having a layer of rod-like liquid crystals, a uniaxial orientation polycarbonate film, and the like.

The defect inspection apparatus 10 transports the film 7 in a transport direction (direction shown with arrow S) through a conveyer mechanism 11. A couple of guide rollers 12 and 13 are placed at a given interval on a transport path of the film 7, and the film 7 is turned around the guide rollers 12 and 13. The guide rollers 12 and 13 rotate along with the movement of the film 7. As being turned around the guide rollers 12 and 13, the film 7 is kept flat in an inspection stage between the guide rollers 12 and 13.

A light source 15, a light receiver 16, a first polarizing plate 18, and a second polarizing plate 19 are placed in the inspection stage. The light source 15 and the light receiver 16 are placed at both sides of the film 7 to face to each other.

In this embodiment, the light source 15 is placed below the transport path so as to uniformly project light toward the bottom side of the film 7 through the first polarizing plate 18. The light source 15 converts light of a halogen lamp into linear light through a quartz light guide or a plastic light guide, and projects the linear light toward an inspection area 17. As described in detail later, the light source 15 is inclined to a widthwise direction (direction shown with arrow M) of the film 7, and so is the inspection area 17. Note that the configuration of the light source 15 is not limited to this.

The light receiver 16 is placed above the transport path so as to photoelectrically detect the inspection area 17 on the film 7 through the second polarizing plate 19. The light receiver 16 is constituted of a linear array camera, which has a taking lens 16a and a line image sensor 16b consisting of a large number of photo sensors arranged in a line. The light receiver 16 takes an image of the inspection area 17 one line at a time through the second polarizing plate 19 each time a given length of the film 7 is conveyed. Thereby, the light receiver 16 converts light component that has passed through the second polarizing plate 19 after being projected through the inspection area 17 into an electric detection signal.

The first polarizing plate 18 is placed between the light source 15 and the film 7, whereas the second polarizing plate 19 is placed between the film 7 and the light receiver 16. The first and second polarizing plates 18 and 19 are placed parallel to surfaces of the film 7. For this configuration, the light from the light source 15 is projected to the film 7 through the first polarizing plate 18, and the light receiver 16 receives the light having passed through the second polarizing plate 19.

Figure 2:
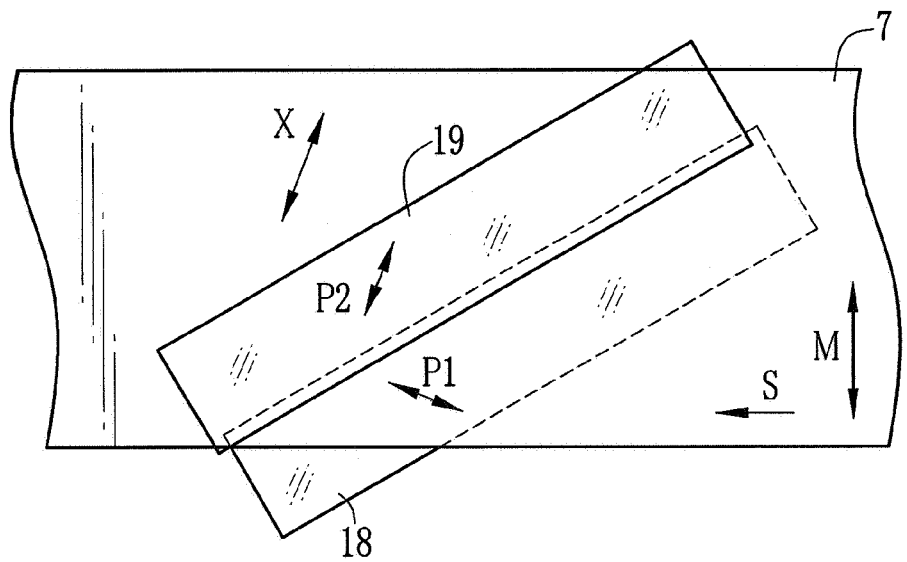
FIG. 2 is an explanatory diagram illustrating a relation between polarizing transmission axes of polarizing plates and a relation between the polarizing transmission axes and a slow axis of a film to be inspected.

The first and second polarizing plates 18 and 19 are both linear polarization type. As shown in FIG. 2, the first and second polarizing plates 18 and 19 are placed to be crossed nicols in which a polarizing transmission axis P1 of the first polarizing plate 18 and a polarizing transmission axis P2 of the second polarizing plate 19 are perpendicular to each other. In addition, the first and second polarizing plates 18 and 19 are arranged such that one of the polarizing transmission axes P1 and P2 is approximately parallel to a slow axis X of the film 7. In this embodiment, the polarizing transmission axis P2 of the second polarizing plate 19 is approximately parallel to the slow axis X of the film 7. The slow axis X indicates a direction with highest refractive index.

Note that the polarizing transmission axis and the slow axis X need not be precisely parallel to each other. Since there is 0° to 5° angular difference between the slow axis X and the rubbing angle for molecular orientation of the liquid crystal layer, the polarizing transmission axis and the slow axis X can have the angular difference within the range of 0° to 5°. In addition, the first and second polarizing plates 18 and 19 that are placed to be crossed nicols need not be precisely perpendicular to each other, but the angular difference thereof is preferably within about ±2°.

The lower the orthogonal transmittance of the first and second polarizing plates 18 and 19 being placed to be crossed nicols, the more accurately the defects with low brightness, that is, fine defects are detected. The film 7 is interposed between the first and second polarizing plates 18 and 19 in crossed nicols. Average orthogonal transmittance of the polarizing plates 18 and 19 to light having wavelength of 500 nm to 750 nm is preferably not more than 0.027%. Orthogonal transmittance of the polarizing plates 18 and 19 to light having wavelength of 750 nm is not more than 0.030%. With use of such polarizing plates, defects with low brightness can be detected, which is preferable.

The detection signal from the light receiver 16 is sent to a judgment section 21. The judgment section 21 performs various signal processing such as enhancement processing to the detection signal, and judges based on the changes of the detection signal as to whether there is a defect in the film. The guide roller 13 is equipped with an encoder 22 that generates an encode pulse signal each time a given length of the film 7 is conveyed. The judgment section 21 identifies a location of the detected defect of the film 7 based on the encode pulse signal from the encoder 22 and a detection signal of one line that includes the defect, and generates position data indicating lengthwise and widthwise positions of the defect in the film 7. The position data is output to an output device 23 and sent to a later process. In this embodiment, the output device 23 is a monitor, and the position data is displayed on the monitor. In the later process, a portion of the film 7 including the defect is discarded based on the position data.

Figure 3:
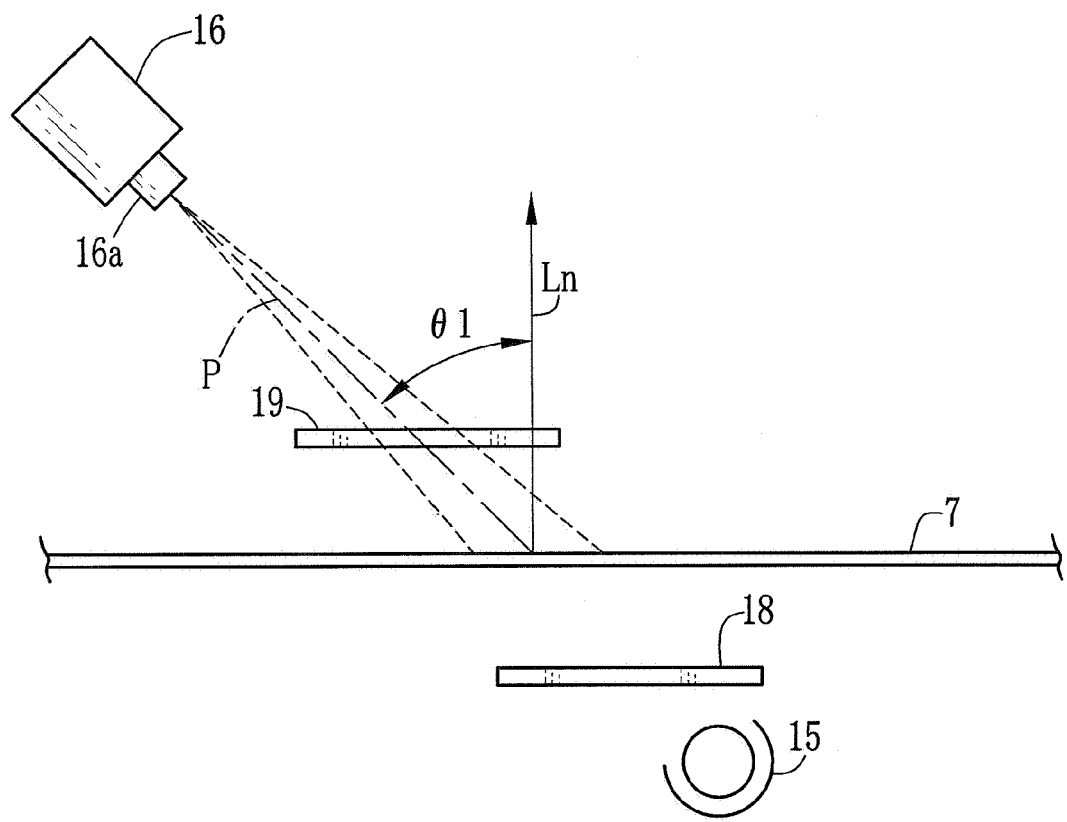
FIG. 3 is an explanatory diagram illustrating a cross angle θ1 of a light receiver.
Figure 4:
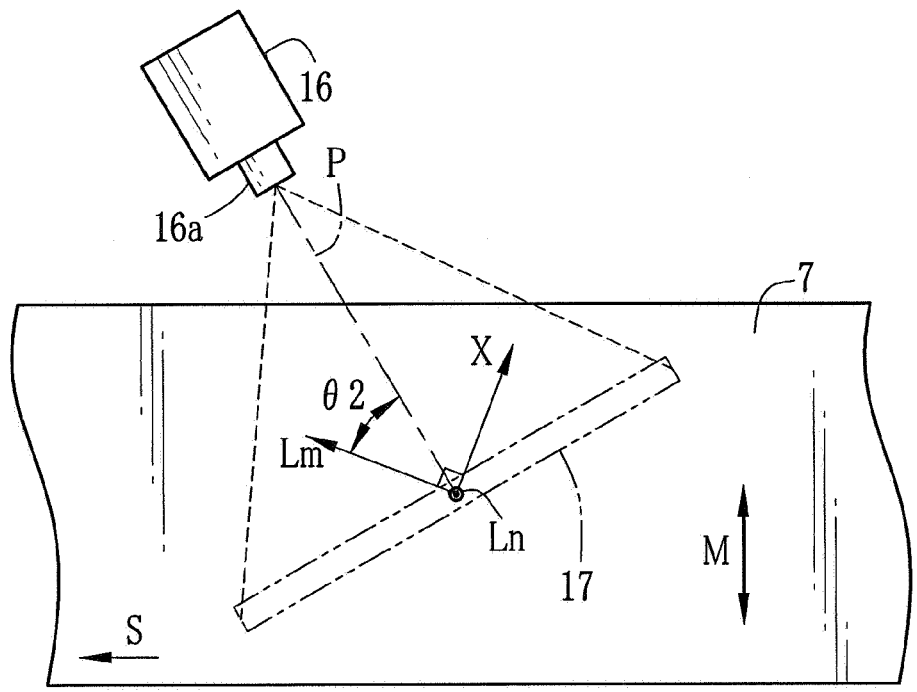
FIG. 4 is an explanatory diagram illustrating a rotational angle θ2 of the light receiver.

FIGS. 3 and 4 are the diagrams showing a light receiving position of the light receiver 16 with respect to the film 7 to be inspected. As shown in FIG. 3, the light receiver 16 is placed to look down the film 7 and such that an optical axis P of the light receiver 16 and a normal line Ln of the film surface in the inspection area 17 forms an angle θ1. The angle θ1 is preferably within the range of 15° to 35°, and more preferably within the range of 20 to 25°. As shown in FIG. 4, seen from above the film 7, the light receiver 16 is also rotated horizontally around the normal line Ln, such that a rotational angle θ2 is formed between the optical axis P and a reference line Lm that is orthogonal to the slow axis X. The rotational angle θ2 is preferably within the range of 20° to 60°, and more preferably within the range of 30° to 60°.

Note that the angle θ1 is an angle between optical axis P and the normal line Ln on the vertical plane of the film 7 (hereinafter referred to as cross angle). The rotational angle θ2 is an angle between the optical axis P and the reference line Lm on the horizontal plane of the film 7, that is, an angle between the reference line Lm and an orthogonal projection of the optical axis P on the surface of the film 7.

When the cross angle θ1 and the rotational angle θ2 are in the above-mentioned ranges, S/N ratio (signal intensity ratio) of the detection signals output from the light receiver 16 is raised. Owing to this, fine defects or defects with low brightness can be reliably detected.

Defects to be detected have directional properties and lengths that extend, for example, in the transport direction or the widthwise direction of the film 7. Portions not including the defects of the film 7 (hereinafter referred to as texture) also have certain directional properties and lengths. In order to distinguish the defect and the texture of the film 7, the defect portion needs to be obtained as a serial signal. When the S/N ratio of the detection signals is raised, it facilitates distinguishing the noise in the detection signal of the light having passed through the normal texture portion and received on the light receiver 16, from the detection signal of the light having passed through the defect portion and received on the light receiver 16. Hereinafter, the light passed through the texture portion is referred to as texture detection light, and the light passed through the defect portion is referred to as defect detection light.

When the S/N ratio of the detection signals from the light receiver 16 is lower than 2.0, it is hard to distinguish the normal texture portion from the defect portion no matter what distinguishing devices are used or no matter what signal processing is performed. The S/N ratio should be not less than 2.0 as a practical level. The cross angle θ1 and the rotational angle θ2 are designated within the above-mentioned ranges so as to obtain the S/N ratio of not less than the practical level.

Figure 5:
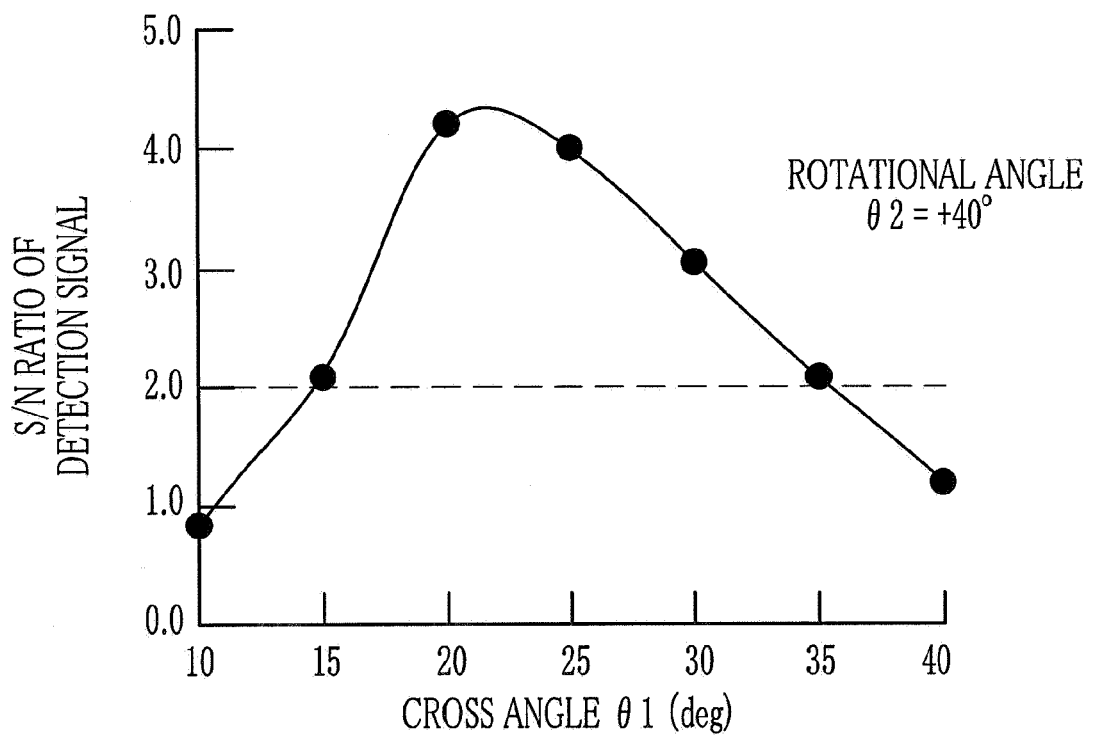
FIG. 5 is a graph illustrating the changes of detection signal intensity as the cross angle θ1 changes.
Figure 6:
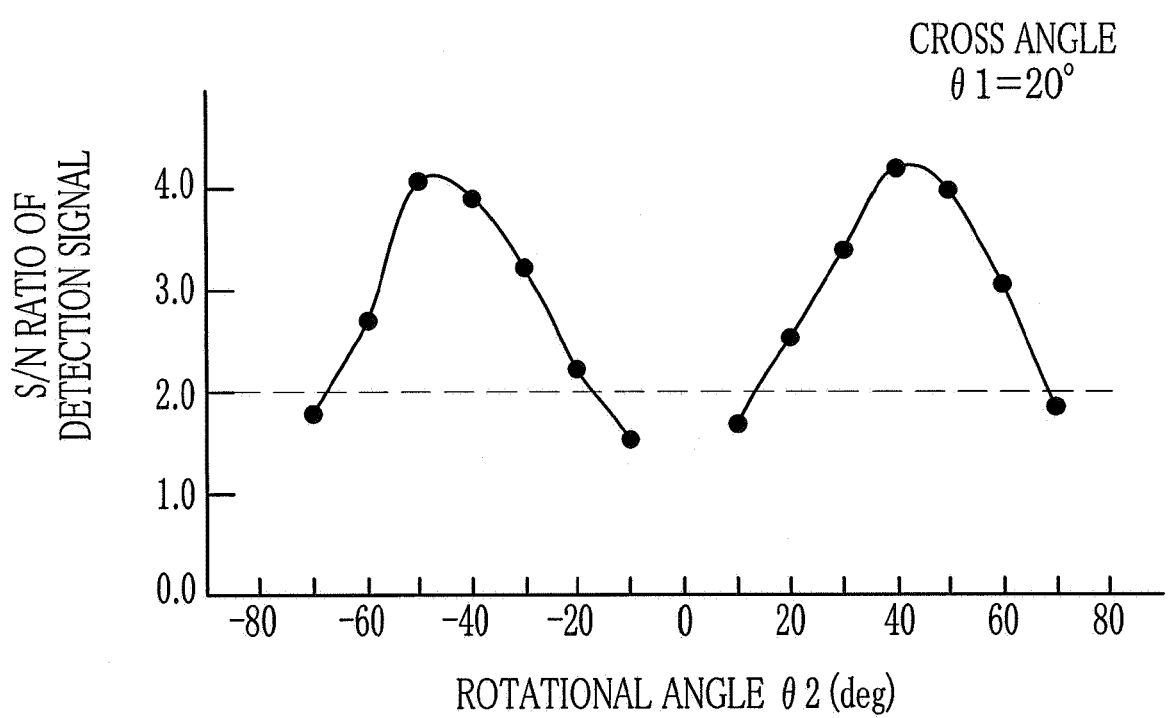
FIG. 6 is a graph illustrating the changes of detection signal intensity as the rotational angle θ2 changes.

In FIG. 5, the changes of the S/N ratio of the detection signals at the time of detecting defects while changing the cross angle θ1 are illustrated. At this time, the rotational angle θ2 is constant (θ2=+40°). In FIG. 6, the changes of the S/N ratio of the detection signals at the time of detecting defects while changing the rotational angle θ2 are illustrate. At this time, the cross angle θ1 is constant (θ1=20°).

As shown in FIG. 5, when defects are detected while the rotational angle θ2 is constant and the cross angle θ1 changes, the S/N ratio of the detection signals changes according to increase and decrease of the cross angle θ1. When the cross angle θ1 is within the range of 15° to 35°, the S/N ratio of the detection signals becomes not less than the practical level (S/N ratio=2.0). Moreover, when the cross angle θ1 is within the range of 20° to 25°, the S/N ratio of the detection signals is sufficiently raised, which enables detecting defects with extremely low brightness (defect rank 4, which is described later).

That is, the cross angle θ1 within the range of 15° to 35° raises intensity of the defect detection light compared to the texture detection light, which enables fully distinguishing the defect detection light from the texture detection light. Moreover, the cross angle θ1 within the range of 20° to 25° enables distinguishing extremely weak defect detection light. When the cross angle θ1 is smaller than 15°, the intensity of the texture detection light becomes weak, and at the same time, the intensity of the defect detection light also becomes weak. When the cross angle θ1 is larger than 35°, the intensity of the texture detection light becomes strong, and at the same time, the intensity of the defect detection light also becomes strong. In either case, it is hard to distinguish the defect detection light from the texture detection light.

As shown in FIG. 6, when defects are detected while the cross angle θ1 is constant and the rotational angle θ2 changes, the S/N ratio of the detection signals changes according to increase and decrease of the rotational angle θ2. When the rotational angle θ2 is within the range of −60° to −20° or +20° to +60°, the S/N ratio of the detection signals becomes not less than the practical level (S/N ratio=2.0) enough for reliably detecting defects. Moreover, when the rotational angle θ2 is within the range of −60° to −30° or +30° to +60°, the S/N ratio of the detection signals is sufficiently raised, which enables detecting defects with extremely low brightness (defect rank 4). Note that "positive" of the rotational angle θ2 indicates a counterclockwise rotation from the reference line Lm in FIG. 4, and "negative" of the rotational angle θ2 indicates a clockwise rotation from the reference line Lm in FIG. 4.

In order to accurately detect defects, the cross angle θ1 is set within the range of 15° to 35°, and the rotational angle θ2 is set within the range of 20° to 60°, and more preferably, the cross angle θ1 is set within the range of 20° to 25°, and the rotational angle θ2 is set within the range of 30° to 60°. When the cross angle θ1 is large, slope of the detection signal for one line becomes large (steep) due to angular dependence. This affects the detection of the defects in the inspection area 17. Accordingly, the cross angle θ1 is especially preferably 20°.

Since the reference line Lm as a reference of the rotational angle θ2 can be set at 90° from the slow axis X in both the clockwise direction and the counterclockwise direction, there are four points (areas) in total on both directions that satisfy the above-mentioned angular range. When the light receiver 16 is placed at any one of these four points, the defect inspection can be performed. In order to detect defects more accurately, the light receiver 16 should be placed on the direction to have higher amount of the transmitted light from the film 7.

Figure 7A:
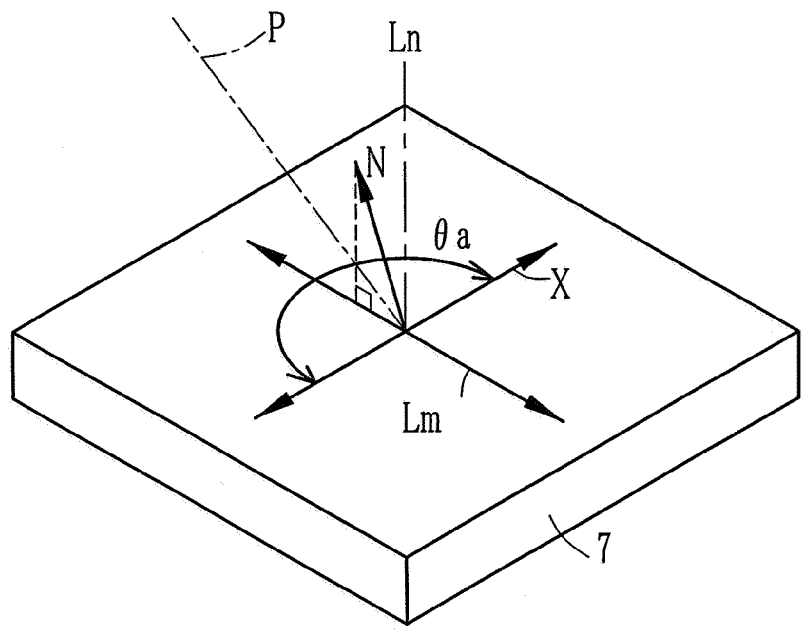
FIG. 7A is an explanatory diagram illustrating a preferable range of the rotational angle θ2 of the light receiver when the film to be inspected is a negative uniaxial birefringence film.

That is, when the film 7 is the negative uniaxial birefringence film, the light receiver 16 is placed at the rotational angle θ2 within an area θa, as shown in FIG. 7A. The area θa resides on the same side, from the slow axis X of the film 7, as an optic axis N of the film being orthogonally projected.

Figure 7B:
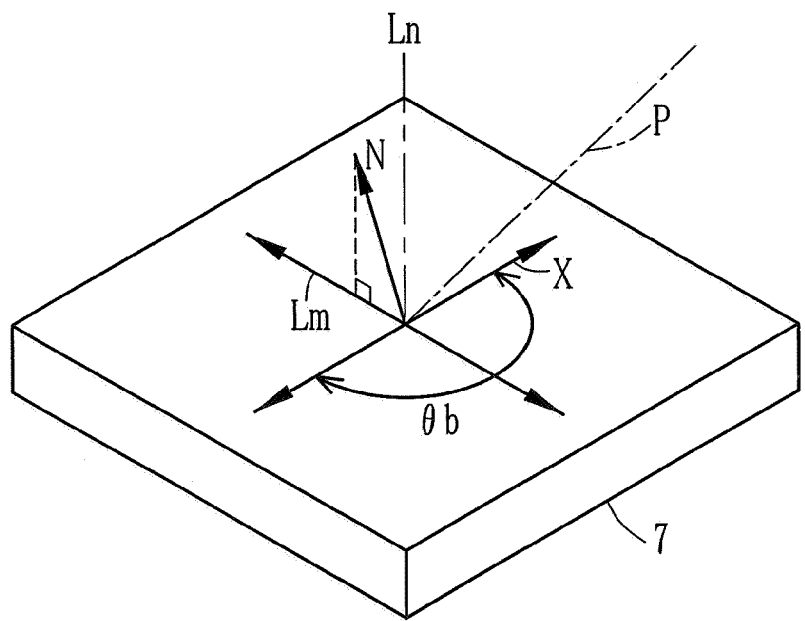
FIG. 7B is an explanatory diagram illustrating a preferable range of the rotational angle θ2 of the light receiver when the film to be inspected is a positive uniaxial birefringence film.

When the film 7 is the positive uniaxial birefringence film, the light receiver 16 is placed at the rotational angle θ2 within an area θb, as shown in FIG. 7B. The area θb is opposite to the area θa with the slow axis X as a boundary. That is, the area θb resides on the opposite side, from the slow axis X of the film 7, as the optic axis N of the film being orthogonally projected.

Figure 8:
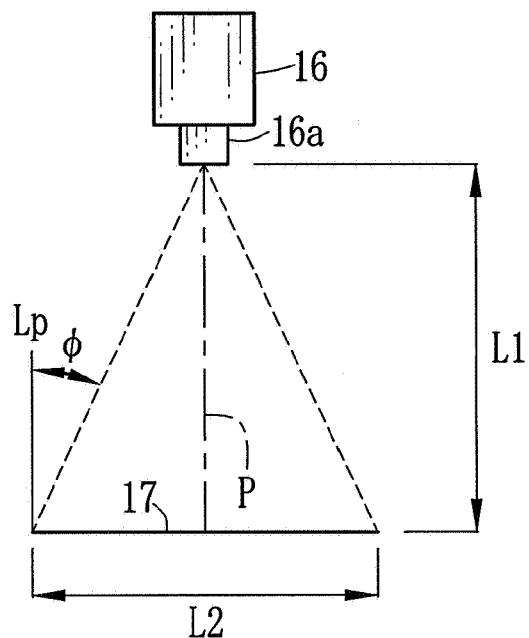
FIG. 8 is an explanatory diagram illustrating a maximum angle Φ.

As shown in FIG. 8, a light receiving distance L1 between the light receiver 16 and the film 7 is adjusted in accordance with a focal length of the taking lens 16a so that the inspection area 17 is adjusted to have a predetermined inspection width L2 (in this embodiment, 250 mm). The light receiving distance L1 is preferably long by making the focal length of the taking lens 16a long so that a maximum angle Φ, which is formed between the optical axis P and a line that connects the taking lens 16a with one of longitudinal ends of the inspection area 17, becomes as small as possible. The maximum angle Φ is preferably in the range of 3° to 10°, and more preferably in the range of 3° to 5°. Note that the maximum angle Φ is illustrated as an angle formed between the line that connects the taking lens 16a with one of longitudinal ends of the inspection area 17 and a straight line Lp parallel to the optical axis P for the sake of explanation in FIG. 8.

The maximum angle Φ is set within the above-mentioned range so that defects can be accurately detected with less affect of the angular dependence when the light receiver 16 is used to receive light from the film such as the film 7 having the birefringence properties.

Figure 9A:
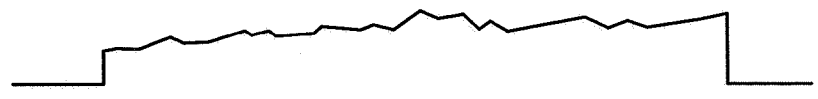
FIGS. 9A, 9B and 9C are explanatory diagrams each illustrating slope of a detection signal with respect to the maximum angle Φ.
Figure 9B:
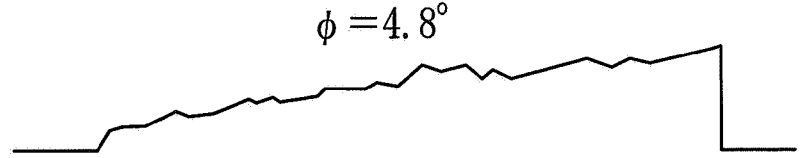
Figure 9C:
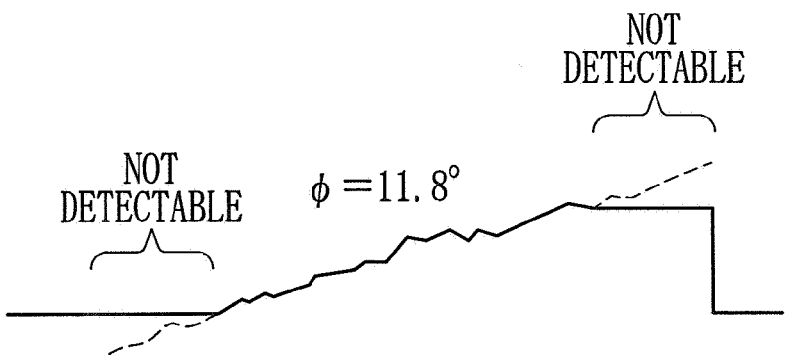

FIGS. 9A, 9B and 9C illustrate examples of the detection signals for one line corresponding to the inspection area 17. In FIG. 9A, the maximum angle Φ is 3.2°. In FIG. 9B, the maximum angle Φ is 4.8°. In FIG. 9C, the maximum angle Φ is 11.8°. Relation between the focal length of the taking lens 16a and the light receiving length L1 between the light receiver 16 and the film 7 for each maximum angle Φ is shown in Table 1. In either case, the inspection width L2 of the inspection area 17 is 250 mm.

TABLE 1

| FOCAL LENGTH OF TAKING LENS (mm) | LIGHT RECEIVING LENGTH (mm) | VIEWING ANGLE (deg) |
|---|---|---|
| 200 | 2250 | 3.2 |
| 135 | 1500 | 4.8 |
| 55 | 615 | 11.8 |

Inspection width L2 = 250 mm

Level of the detection signal for one line output from the light receiver 16 is not constant, but has slope in which the signal level is low at one edge side of the inspection area 17 and high at the other edge side of the inspection area 17. The detection signal has such slope due to the influence of the angular dependence under the condition that the cross angle θ1 and the rotational angle θ2 are given to the light receiver 16. One edge side of the inspection area 17 is observed as a dark area and the other edge side of the inspection area 17 is observed as a bright area by the light receiver 16. Steep slope of the detection signal indicates large difference of brightness between the dark area and the bright area.

As shown above, the slope of the detection signal changes according to the maximum angle Φ. The slope becomes steeper as the maximum angle Φ becomes larger. However, when the maximum angle Φ is larger than a certain value, the difference of brightness between the dark area and the bright area observed with the light receiver 16 exceeds latitude of the light receiver 16. Then, the edge portions cannot be detected as the signal variation, or the signal level variation of the defect cannot be detected due to the restriction of the latitude. For this reason, the range of the maximum angle Φ is set as described above.

Now the operation of the defect inspection apparatus 10 is described. The film 7 to be inspected, the retardation film manufactured through the devices 4 and 5 in this embodiment, is sent to the defect inspection apparatus 10, and is conveyed one way through the inspection stage. While the film 7 is being conveyed, the light source 15 projects light through the first polarizing plate 18 onto the film 7, so the light receiver 16 takes a line of image each time a given length of the film 7 is conveyed.

Every line of image taken by the light receiver 16 is output as a photoelectric signal, and is sequentially sent to the judgment section 21. The judgment section 21 judges as to whether there is any defect, and specifies the location of the defect if there is any defect. The detection signal has a higher value at the defective portion of the film 7 than at the normal portions. So the judgment section 21 judges the higher signal as a defect, and position data of the defect in the lengthwise and widthwise directions of the film 7 is output by the output device 23. The position data is also sent to the later process.

As described above, the light is projected onto the film through the first polarizing plate 18 and the light component having passed through the second polarizing plate 19 is received on the light receiver 16 that is positioned at the above-mentioned cross and rotational angles θ1 and θ2. Since the judgment as to whether there is a defect is made based on the detection signals obtained from the light received on the light receiver 16, fine defects are accurately detected.

Figure 10:
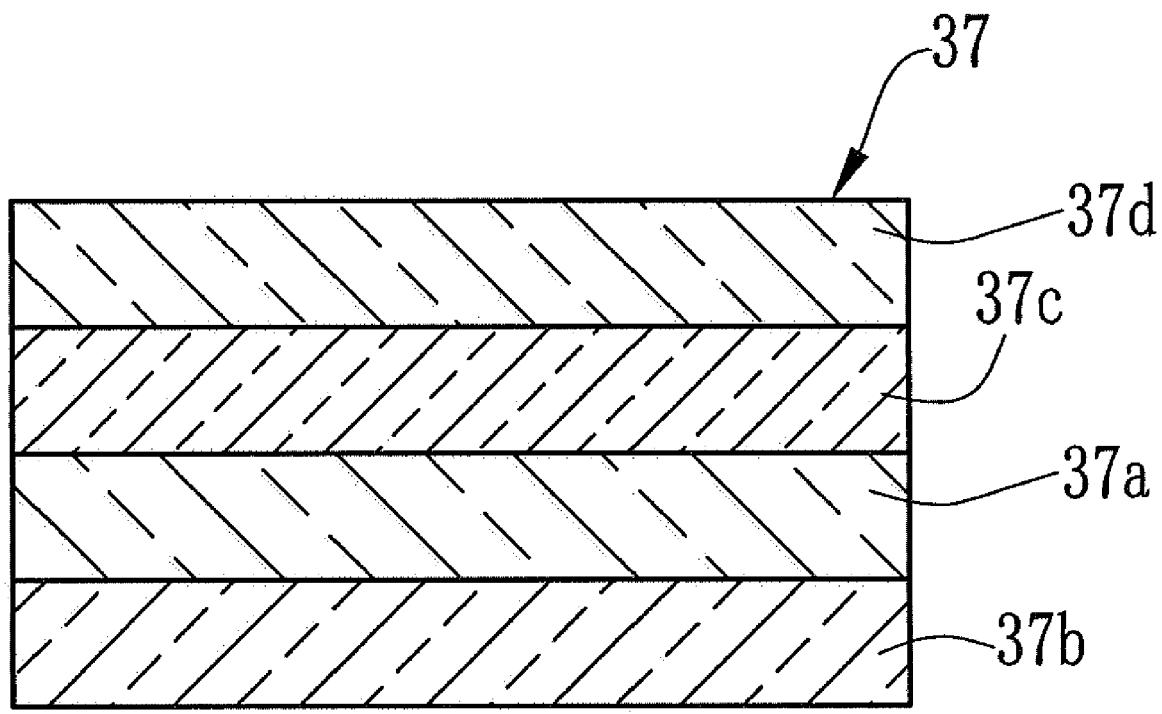
FIG. 10 is a sectional view illustrating a film having a polarizing layer formed on one surface thereof.

Next, a second embodiment of the present invention is explained. Besides the descriptions given below, components identical to those of the first embodiment are denoted by the same reference numerals, and descriptions thereof are omitted. As shown in FIG. 10, a film 37 to be inspected is constituted of a transparent base film 37a having a liquid crystal layer 37b formed on one side thereof and a polarizing layer 37c formed on the other side thereof. A transparent protection film 37d is formed on an exposed surface of the polarizing layer 37c. The combination of the base film 37a and the liquid crystal layer 37b is equivalent to the film 7 of the first embodiment, and is a positive or negative uniaxial birefringence film whose optic axis is inclined with respect to a normal line of the film surface.

To produce the film 37, for example, a polarizing film to be the polarizing layer 37c is produced by staining a polyvinyl alcohol (PVA) film with iodine and stretching it. The protection film 37d is attached on the surface of the polarizing film. The base film 37a having the liquid crystal layer 37b formed thereon is attached to the polarizing film, thereby forming the film 37. Note that the producing method of the film 37 is not limited to this.

Figure 11:
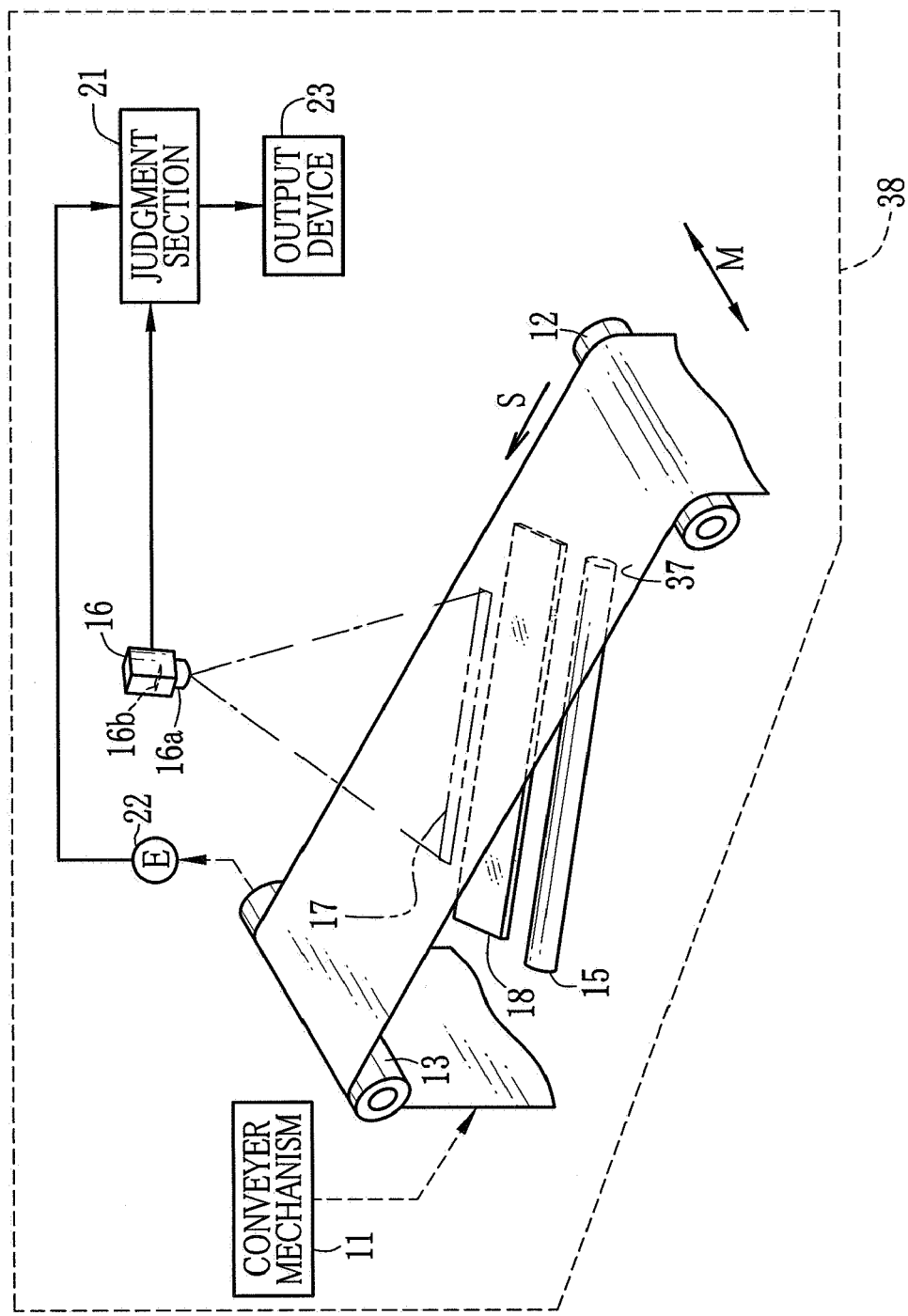
FIG. 11 is a schematic diagram illustrating a defect inspection apparatus for detecting defects in the film having the polarizing layer formed on one surface thereof.

In FIG. 11, a defect inspection apparatus 38 for detecting defects of the film 37 is shown. The defect inspection apparatus 38 is provided with the first polarizing plate 18, but not provided with the second polarizing plate 19 since the polarizing layer 37c of the film 37 is used as one of the polarizing members. The film 37 is conveyed through the inspection stage while the polarizing layer 37c faced upward. At this time, the direction of the polarizing transmission axis of the first polarizing plate 18 is designated such that the polarizing layer 37c and the first polarizing plate 18 are placed to be crossed nicols.

The polarizing transmission axis of one of the polarizing layer 37c and the first polarizing plate 18 is approximately parallel to a slow axis of the film 37. When the film 37 is produced according to the method described above, usually, the polarizing transmission axis of the polarizing layer 37c and the slow axis of the film 37 are substantially parallel. Therefore, the direction of the polarizing transmission axis of the first polarizing plate 18 is designated accordingly. When the polarizing transmission axis of the polarizing layer 37c and the slow axis of the film 37 are perpendicular to each other, the first polarizing plate 18 is placed such that the direction of the polarizing transmission axis of the first polarizing plate 18 becomes parallel to the slow axis of the film 37.

Conditions of the cross angle $\theta 1$, the rotational angle $\theta 2$, and the maximum angle $\Phi$, which is formed between the optical axis P and the line that connects the taking lens 16a with one of longitudinal ends of the inspection area 17, are same as those of the first embodiment. When the first polarizing plate 18 is placed on the side of the liquid crystal layer 37b of the film 37 so as to be crossed nicols with the polarizing layer 37c, like the first and second polarizing plates 18 and 19 of the first embodiment, average orthogonal transmittance of the first polarizing plate 18 and the polarizing layer 37c to light having wavelength of 500 nm to 750 nm is preferably not more than 0.027%. Orthogonal transmittance of the first polarizing plate 18 and the polarizing layer 37c to light having wavelength of 750 nm is not more than 0.030%. Such polarizing plate and the polarizing layer are preferably used.

For this configuration, defects of the film 37 can be detected in the same manner as the first embodiment. The film 37 is not limited to the film having the liquid crystal layer formed thereon, as long as the film has the positive or negative uniaxial birefringence properties.

EXAMPLES

In Examples 1, 2, 3 and 4, the defect inspection apparatus 10 of the first embodiment was used. A retardation film that is used as a transparent optical compensation film was produced, as the film 7 to be inspected, by the above-described devices 4 and 5. Defects, which are generated due to the localized misalignment of the optic axis of the liquid crystal layer, were detected with use of polarizing plates A, B, C and D of different orthogonal transmittances as the first and second polarizing plates 18 and 19. In each Example, same kind of polarizing plates were used as the first and second polarizing plates 18 and 19.

Figure 12:
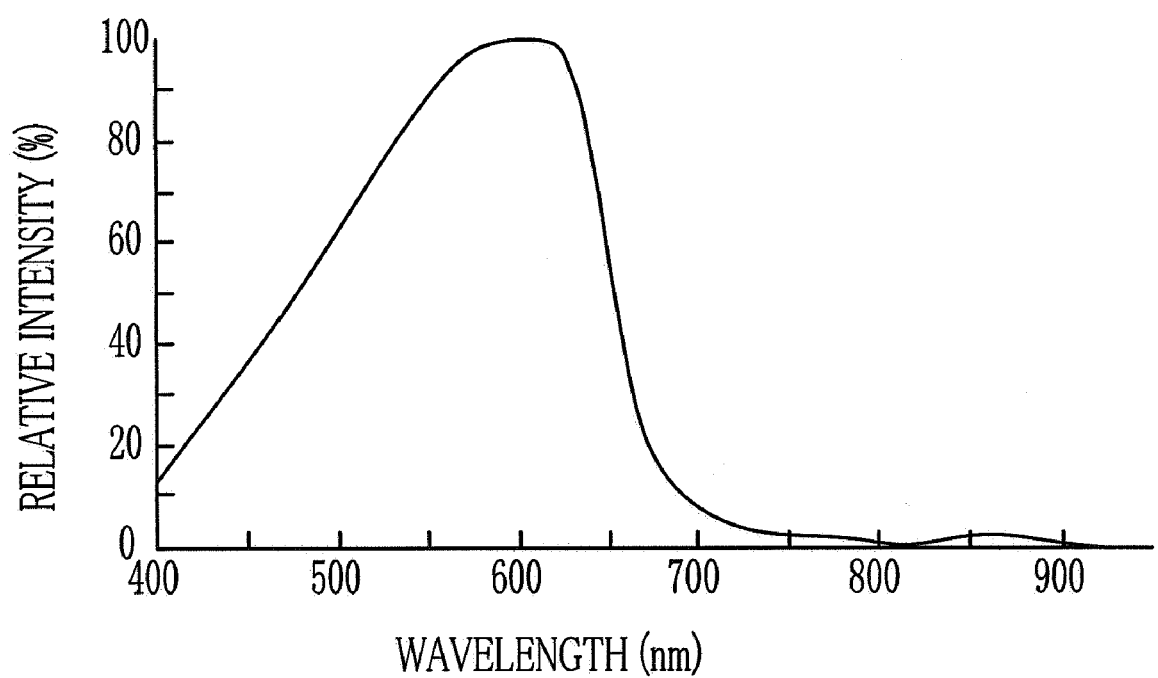
FIG. 12 is a graph illustrating spectral distribution of the light source when a defect is detected with the defect inspection apparatus of the present invention.

In Examples 1 to 4, the cross angle $\theta 1$ was 20° and the rotational angle $\theta 2$ was 40°. The light source 15 was a combination of a halogen lamp and a light guide. The spectral distribution of the light source 15 was as shown in FIG. 12.

Figure 13:
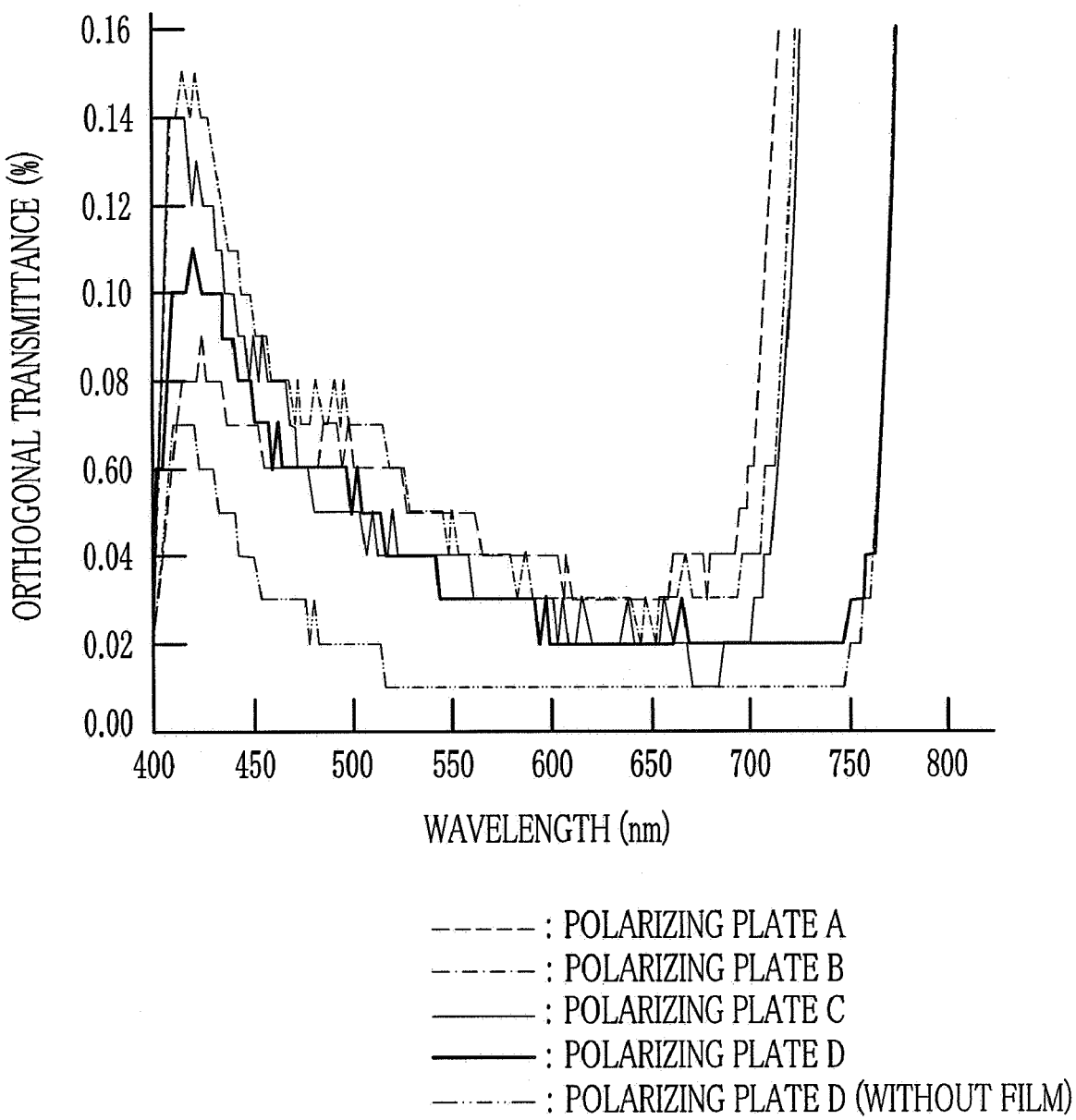
FIG. 13 is a graph illustrating wavelength distribution characteristics of orthogonal transmittance of each polarizing plate used in Examples of the present invention.
Figure 14:
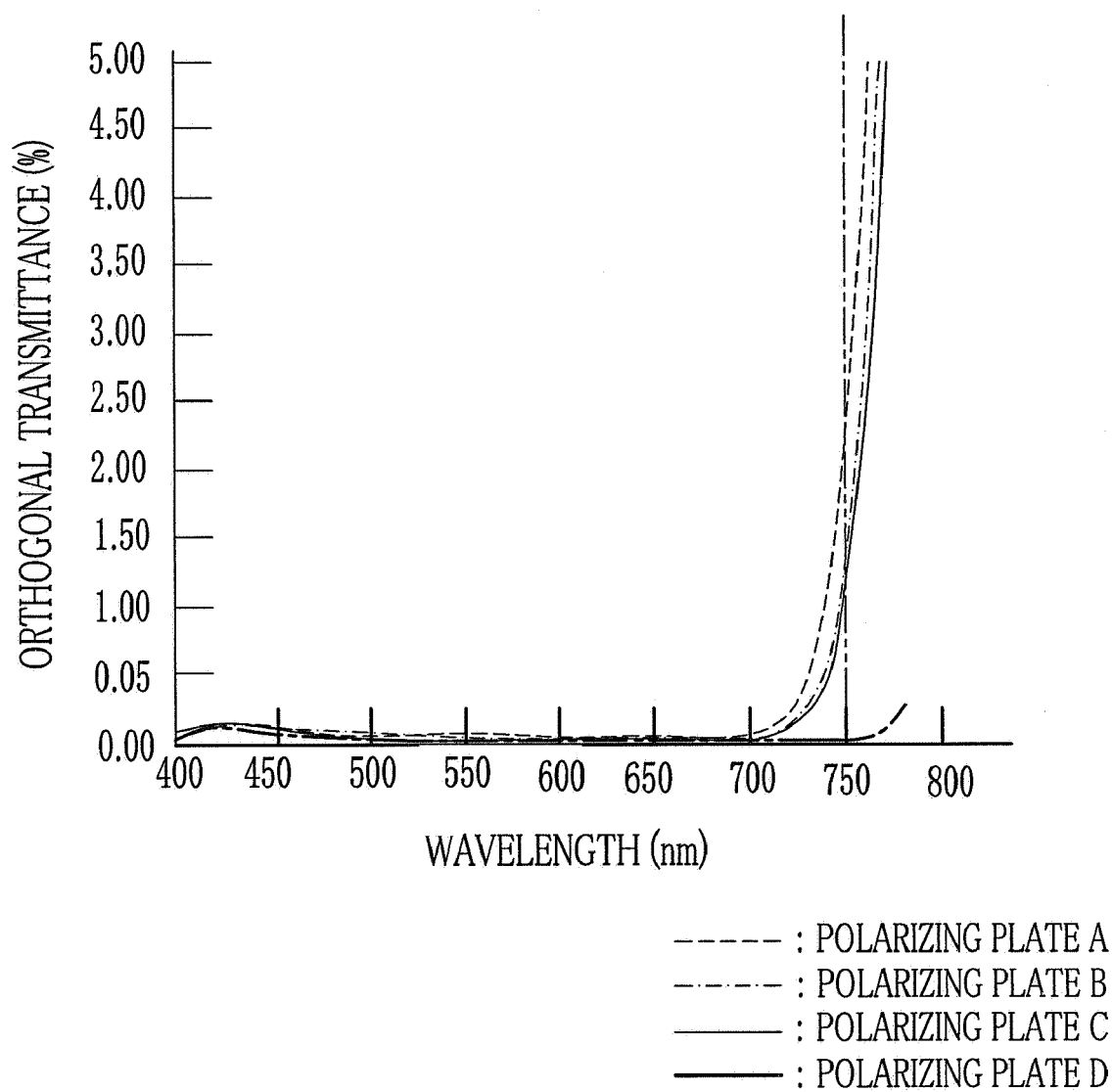
FIG. 14 is a graph same as the one illustrated in FIG. 13 but on a different scale.

The wavelength distribution characteristics of orthogonal transmittance of each polarizing plates pair A to D is shown in a graph of FIG. 13. This graph is also shown on a different scale in FIG. 14, for the sake of clarifying the difference of the transmittance near the wavelength of 750 nm. Average orthogonal transmittance of each polarizing plates pair A to D to light having wavelength of 500 nm to 750 nm, and orthogonal transmittance of each polarizing plates pair A to D to light having wavelength of 500 nm are shown in Table 2. To measure the orthogonal transmittance for the graphs in FIGS. 13 and 14, and Table 2, the film 7 was interposed between the first and second polarizing plates 18 and 19 in crossed nicols. The first and second polarizing plates 18 and 19 were of the same kind. Note that FIG. 13 also illustrates the orthogonal transmittance of the polarizing plates pair D without interposing the film 7 therebetween.

TABLE 2

| POLARIZING PLATE | ORTHOGONAL TRANSMISSION *1 (%) | ORTHOGONAL TRANSMISSION *2 (%) |
| --- | --- | --- |
| A | 0.165 | 2.38 |
| B | 0.099 | 1.25 |
| C | 0.092 | 1.39 |
| D | 0.027 | 0.03 |

*1 value to light having wavelength of 500 nm to 750 nm
*2 value to light having wavelength of 750 nm As Comparative Examples 1 and 2, defects were detected by the method disclosed in United States Patent Application Publication No. US 2001/0021016 (corresponding to Japanese Patent Laid-open Publication No. 2001-324453) with use of the polarizing plates pairs A used in Example 1 and D used in Example 4. That is, the film 7 was interposed between the pair of the polarizing plates A or the pair of the polarizing plates D. The polarizing plates were placed parallel to the film 7 interposed therebetween. One of the polarizing plates was placed such that its polarizing transmission axis and the slow axis of the film 7 forms an adequate intersection angle. An optical compensation film practically equivalent to the film 7 was placed between the film 7 and one of the polarizing plates. Light was received with a CCD camera in a normal line direction of the film surface. Note that the intersection angle formed between the slow axis of the film 7 and the polarizing transmission axis of one of the polarizing plates was 15°. The optical compensation film between the polarizing plate and the film 7 was rotated through 180° along a plane corresponding to the film surface. The light source was the same as used in Examples 1 to 4.

Figure 15:
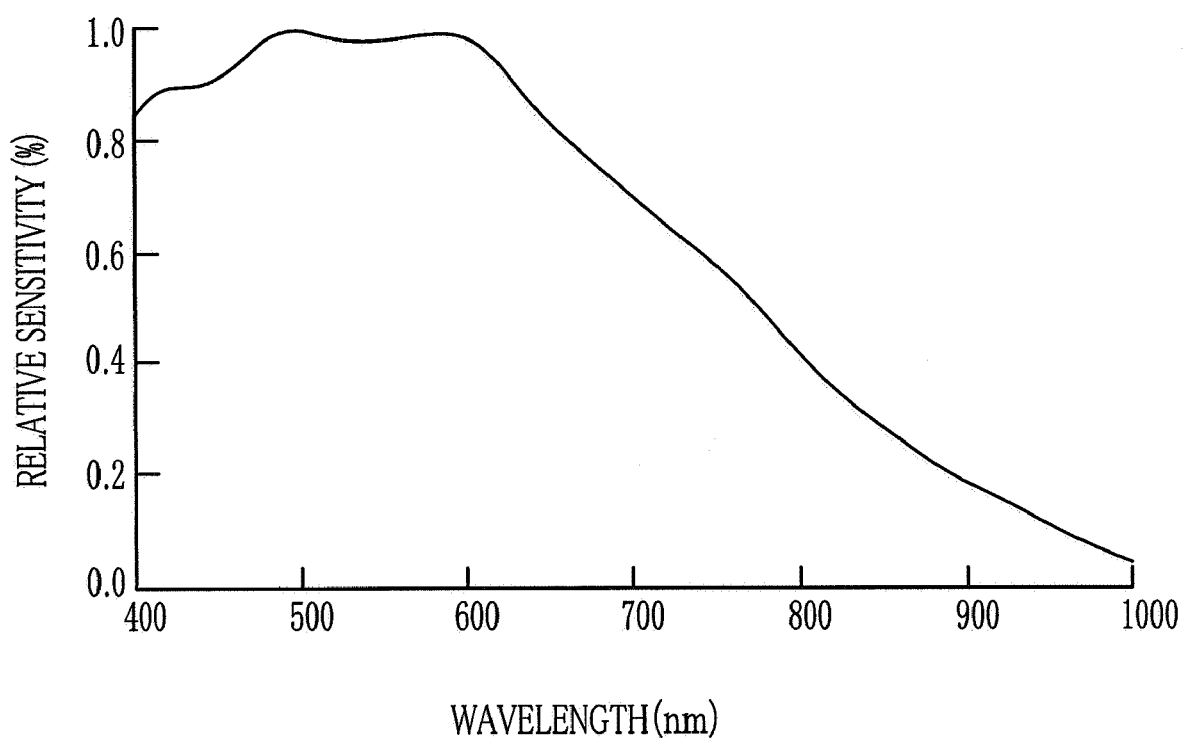
FIG. 15 is a graph illustrating spectral sensitivity characteristics of a CCD line sensor used in Examples of the present invention.

In Examples 1 to 4, a monochrome CCD line sensor was used as the light receiver 16. In Comparative Examples 1 and 2, the CCD line sensor used as the light receiver 16 in Examples 1 to 4 was used as a CCD camera. Spectral sensitivity characteristics of this CCD line sensor is as shown in FIG. 15.

Detection results of Examples 1 to 4 and Comparative Examples 1 and 2 are shown in Table 3. Defect ranks 1, 2, 3 and 4 represent degrees of the defect according to the difference in contrasting density (brightness) between the defective portion and its surroundings. The defect rank 1 has largest difference in the contrasting density, and the difference becomes smaller as the rank 2, 3 and 4, in this order.

TABLE 3

|  | Ex. 1 (A)[1] | Ex. 2 (B)[1] | Ex. 3 (C)[1] | Ex. 4 (D)[1] | Com. Ex. 1 (A)[1] | Com. Ex. 2 (D)[1] |
| --- | --- | --- | --- | --- | --- | --- |
| DEFECT RANK 1 | D[2] | D | D | D | ND[3] | ND |
| DEFECT RANK 2 | D | D | D | D | ND | ND |
| DEFECT RANK 3 | ND | ND | ND | D | ND | ND |
| DEFECT RANK 4 | ND | ND | ND | D | ND | ND |

Examples 1-4: cross angle θ1 = 20°, rotational angle θ2 = 40°
Comparative Examples 1 and 2: intersection angle = 15°
[1] polarizing plate
[2] Detectable
[3] Not Detectable As can be seen from Table 3 above, defects at rank 1 and 2 could be detected in Examples 1 to 4 of the present invention. In Example 4 in which the polarizing plates pair D whose average orthogonal transmittance to light having wavelength of 500 nm to 750 nm is 0.027% and orthogonal transmittance to light having wavelength of 750 nm is 0.030% was used as the first and second polarizing plates 18 and 19, defects at rank 4 having extremely low defect level were detected. On the contrary, defects at rank 1 to 4 could not be detected in Comparative Example 1 in which the polarizing plates pair A that was used in Example 1 was used, and in Comparative Example 2 in which the polarizing plates pair D that was used in Example 4 was used.

In view of this, it can be understood that the present invention is effective for detecting defects, which are generated due to the localized misalignment of the optic axis of the liquid crystal layer. The lower the average orthogonal transmittance of the first and second polarizing plates 18 and 19 to light having wavelength of 500 nm to 750 nm and the orthogonal transmittance of the same to light having a particular wavelength (750 nm), the more accurately the defects with low brightness can be detected. It is understood that the polarizing plates pair whose average orthogonal transmittance to light having wavelength of 500 nm to 750 nm is not more than 0.027% and orthogonal transmittance to light having wavelength of 750 nm is not more than 0.030% is useful in detecting fine defects. As shown in FIG. 12, when the halogen light source is used as the light source 15, relative intensity of the halogen light source reaches maximum at the wavelength of 550 nm to 630 nm. The halogen light source has the relative intensity at the wavelength of 700 nm to 800 nm as well. Accordingly, the usage of the halogen light source is more suitable in detecting fine defects.

Various changes and modifications are possible in the present invention and may be understood to be within the present invention.

What is claimed is:

1. A defect inspection apparatus for detecting defects of a film comprising:
 a pair of polarizing plates placed to be crossed nicols at both sides of said film, said polarizing plates being parallel to front and rear surfaces of said film, a polarizing transmission axis of one of said polarizing plates being approximately parallel to a slow axis of said film;
 a light source for projecting light onto one of said surfaces of said film through one of said polarizing plates;
 a light receiver placed at an opposite side of said film to said light source, said light receiver firstly receiving the light projected from said light source and transmitted through said film and the other one of said polarizing plates, and then outputting a photoelectric signal corresponding to the received light; and
 a judging device for judging based on the photoelectric signal from said light receiver as to whether there is a defect in said film or not,
 wherein when θ1 represents an angle formed between an optical axis of said light receiver and a normal line that is perpendicular to said surfaces of said film, and θ2 represents a rotational angle formed between said optical axis and a reference line that is orthogonal to said slow axis of said film, said light receiver is positioned to satisfy the following conditions:
 15°≦θ1≦35°, 20°≦θ2≦60°.

2. A defect inspection apparatus as claimed in claim 1, wherein said film is a positive or negative uniaxial birefringence film whose optic axis is inclined with respect to said normal line.

3. A defect inspection apparatus as claimed in claim 1, wherein said film is a positive or negative uniaxial birefringence film having a liquid crystalline compound layer whose optic axis is inclined with respect to said normal line.

4. A defect inspection apparatus as claimed in claim 3, wherein average orthogonal transmittance of said pair of polarizing plates to light having wavelength of 500 nm to 750 nm is not more than 0.027%.

5. A defect inspection apparatus as claimed in claim 4, wherein orthogonal transmittance of said pair of polarizing plates to light having wavelength of 750 nm is not more than 0.030%.

6. A defect inspection apparatus for detecting defects of a film, said film having a polarizing layer formed on one surface thereof, a polarizing transmission axis of said polarizing layer being approximately parallel to a slow axis of said film, said apparatus comprising:
 a polarizing plate placed at an opposite side of said film to said polarizing layer, said polarizing plate being placed to be crossed nicols with said polarizing layer;
 a light source for projecting light onto one surface of said film, or onto the other surface of said film through said polarizing plate;
 a light receiver placed at an opposite side of said film to said light source, said light receiver firstly receiving the light projected from said light source and transmitted through said film and said polarizing plate, or through said film only, and then outputting a photoelectric signal corresponding to the received light; and
 a judging device for judging based on the photoelectric signal from said light receiver as to whether there is a defect in said film or not,
 wherein when θ1 represents an angle formed between an optical axis of said light receiver and a normal line that is perpendicular to said surfaces of said film, and θ2 represents a rotational angle formed between said optical axis and a reference line that is orthogonal to said slow axis of said film, said light receiver is positioned to satisfy the following conditions:
 15°≦θ1≦35°, 20°≦θ2≦60°.

7. A defect inspection apparatus as claimed in claim 6, wherein said film is a positive or negative uniaxial birefringence film whose optic axis is inclined with respect to said normal line.

8. A defect inspection apparatus as claimed in claim 6, wherein said film is a positive or negative uniaxial birefringence film having a liquid crystalline compound layer whose optic axis is inclined with respect to said normal line, said liquid crystalline compound layer being formed on an opposite side of said film to said polarizing layer.

9. A defect inspection apparatus as claimed in claim 8, wherein average orthogonal transmittance of said polarizing layer and said polarizing plate to light having wavelength of 500 nm to 750 nm is not more than 0.027%.

10. A defect inspection apparatus as claimed in claim 9, wherein orthogonal transmittance of said polarizing layer and said polarizing plate to light having wavelength of 750 nm is not more than 0.030%.

11. A defect inspection apparatus as claimed in claim 7, wherein said film is said negative uniaxial birefringence film, said light receiver being placed at said rotational angle $\theta 2$ within an area that resides on the same side, from said slow axis of said film, as an optic axis of said film being orthogonally projected.

12. A defect inspection apparatus as claimed in claim 7, wherein said film is said positive uniaxial birefringence film, said light receiver being placed at said rotational angle $\theta 2$ within an area that resides on the opposite side, from said slow axis of said film, as an optic axis of said film being orthogonally projected.

13. A defect inspection apparatus as claimed in claim 1, wherein said light receiver comprises a taking lens and a line image sensor having a large number of photo sensors arranged in a line, said line of said photo sensors being inclined by said rotational angle $\theta 2$ with respect to said slow axis of said film.

14. A defect inspection apparatus as claimed in claim 13, wherein a maximum angle in the range of 3° to 5° is formed between said optical axis of said light receiver and a line that connects said taking lens with one of longitudinal ends of an inspection area defined on said film.

15. A defect inspection method for detecting defects of a film comprising the steps of:
   projecting light onto one of front and rear surfaces of said film through one of polarizing members, said polarizing members being placed to be crossed nicols at both sides of said film, said polarizing members being parallel to said surfaces of said film, a polarizing transmission axis of one of said polarizing members being approximately parallel to a slow axis of said film;
   receiving the light projected onto and transmitted through said film with use of a light receiver; and
   judging based on the light received on said light receiver as to whether there is a defect in said film or not,
   wherein when $\theta 1$ represents an angle formed between an optical axis of said light receiver and a normal line that is perpendicular to said surfaces of said film, and $\theta 2$ represents a rotational angle formed between said optical axis and a reference line that is orthogonal to said slow axis of said film, said light receiver is positioned to satisfy the following conditions:
   $15° \leq \theta 1 \leq 35°$, $20° \leq \theta 2 \leq 60°$.

* * * * *